(12) United States Patent
Müller et al.

(10) Patent No.: US 6,537,199 B1
(45) Date of Patent: Mar. 25, 2003

(54) ARRANGEMENT FOR MECHANICAL COUPLING OF A DRIVER TO A COUPLING SITE OF THE OSSICULAR CHAIN

(75) Inventors: Gerd M. Müller, Lohhof (DE); Hans Leysieffer, Taufkirchen (DE)

(73) Assignee: Phonak AG, Stafa (CH)

(*) Notice: Subject to any disclaimer, the term of this patent is extended or adjusted under 35 U.S.C. 154(b) by 0 days.

(21) Appl. No.: 09/626,745

(22) Filed: Jul. 26, 2000

(30) Foreign Application Priority Data

Jul. 26, 1999 (DE) .......................................... 199 35 029

(51) Int. Cl.⁷ .............................................. H04R 25/00

(52) U.S. Cl. ...................................................... 600/25

(58) Field of Search ............................ 600/25; 607/55, 607/56, 57, 136, 137; 381/68; 181/128, 129

(56) References Cited

U.S. PATENT DOCUMENTS

| | | |
|---|---|---|
| 3,712,962 A | 1/1973 | Epley |
| 3,870,832 A | 3/1975 | Fredrickson |
| 3,882,285 A | 5/1975 | Nunley et al. |
| 4,850,962 A | 7/1989 | Schaefer |
| 5,015,224 A | 5/1991 | Maniglia |
| 5,015,225 A | 5/1991 | Hough et al. |
| 5,277,694 A | 1/1994 | Leysieffer et al. |
| 5,554,096 A | 9/1996 | Ball |
| 5,624,376 A | 4/1997 | Ball et al. |
| 5,707,338 A | 1/1998 | Adams et al. |
| 5,788,711 A | 8/1998 | Lehner et al. |
| 5,800,336 A * | 9/1998 | Ball et al. ............... 600/25 |
| 5,941,814 A | 8/1999 | Lehner et al. |
| 6,077,215 A | 6/2000 | Leysieffer |
| 6,099,462 A * | 8/2000 | aWengen ................. 600/25 |
| 6,315,710 B1 * | 11/2001 | Bushek et al. ........... 600/25 |

FOREIGN PATENT DOCUMENTS

| | | |
|---|---|---|
| DE | 44 06 081 | 9/1994 |
| DE | 196 47 579 | 5/1998 |
| EP | 0 984 66.3 | 3/2000 |
| EP | 0 984 665 | 3/2000 |
| WO | WO 98/06235 | 2/1998 |
| WO | WO 98/06236 | 2/1998 |
| WO | WO 98/06237 | 2/1998 |
| WO | WO 98/06238 | 2/1998 |
| WO | WO 99/15111 | 4/1999 |

OTHER PUBLICATIONS

H.P. Zenner, et al., Active Electronic Hearing Implants for Labyrinthine and Conduction Deafness—A New Era of Ear Surgery, HNO 1997—vol. 45, Oct. 1997, pp. 749–774.

H. Leysieffer et al., An Implantable Piezoelectric Hearing Aid Converter for Patients with Labyrinthine Deafness, HNO 1997—vol. 45, Oct. 1997, pp. 792–800.

R. Lehner et al., Cold–Flowing Elements for Coupling of an Implantable Hearing Aid Converter to Auditory Ossicle or Perilymph, HNO 1998—vol. 46, Jan. 1998, pp. 27–37.

(List continued on next page.)

*Primary Examiner*—Max F. Hindenburg
*Assistant Examiner*—Brian Szmal
(74) *Attorney, Agent, or Firm*—Nixon Peabody LLP; David S. Safran

(57) ABSTRACT

An implantable arrangement for mechanical coupling of an output driver part of an active or passive hearing system, the driver part being excitable to mechanically vibrate, to a preselected coupling site in the middle or inner ear, such as on the ossicular chain, the footplate of the stapes or the membrane which closes the round window or an artificial window in the cochlea, in the vestibulum or in the labyrinth (equilibrium organ), via a coupling arrangement which has a coupling element which can be connected to the preselected coupling site. The arrangement is provided with an attenuator which adjoins the coupling site in the implanted state and which has entropy-elastic properties.

20 Claims, 7 Drawing Sheets

OTHER PUBLICATIONS

H. Leysieffer et al., Ein Vollständig Implantierbares Hoörsystem Für Innenohrschwerhörige: TICA LZ 3001, HNO 1998, vol. 46, Oct. 1998, pp. 853–863.

H. P. Zenner et al., Erste Implantatonen Eines Vollständig Implantierbaren Elektronischen Hörsystems Bei Patienten Mit Innenohr–Schwerhörigkeit, HNO 1998, vol. 46, Oct. 1998, pp. 844–852.

Anthony J. Maniglia et al., Contactless Semi–Imlantable Electromagnetic Middle Ear Device for the Treatment of Sensorineural Hearing Loss, vol. 28, No. 1, Feb. 1995, pp. 121–141.

John M. Fredrickson et al., Ongoing Investigations into an Implantable Electromagnetic Hearing Aid for Moderate to Severe Sensorineural Hearing Loss, vol. 28, No. 1, Feb. 1995, pp. 107–121.

Naoaki Yanagihara et al., Efficacy of the Partially Implantable Middle Ear Implant in Middle and Inner Ear Disorders, Adv. Audiol., vol. 4, Karger, Basel 1988, pp. 149–159.

Jun–Ichi Suzuki et al., Implantation of Partially Implantable Middle Ear Implant and the Indication, Adv. Audiol., vol. 4, Karger, Basel 1988, pp. 160–166.

ALAA El Seifi, The Necrosed Incus in Stapedectomy Revision, Laryngoscope 106, Apr. 1996, pp. 511–512.

* cited by examiner

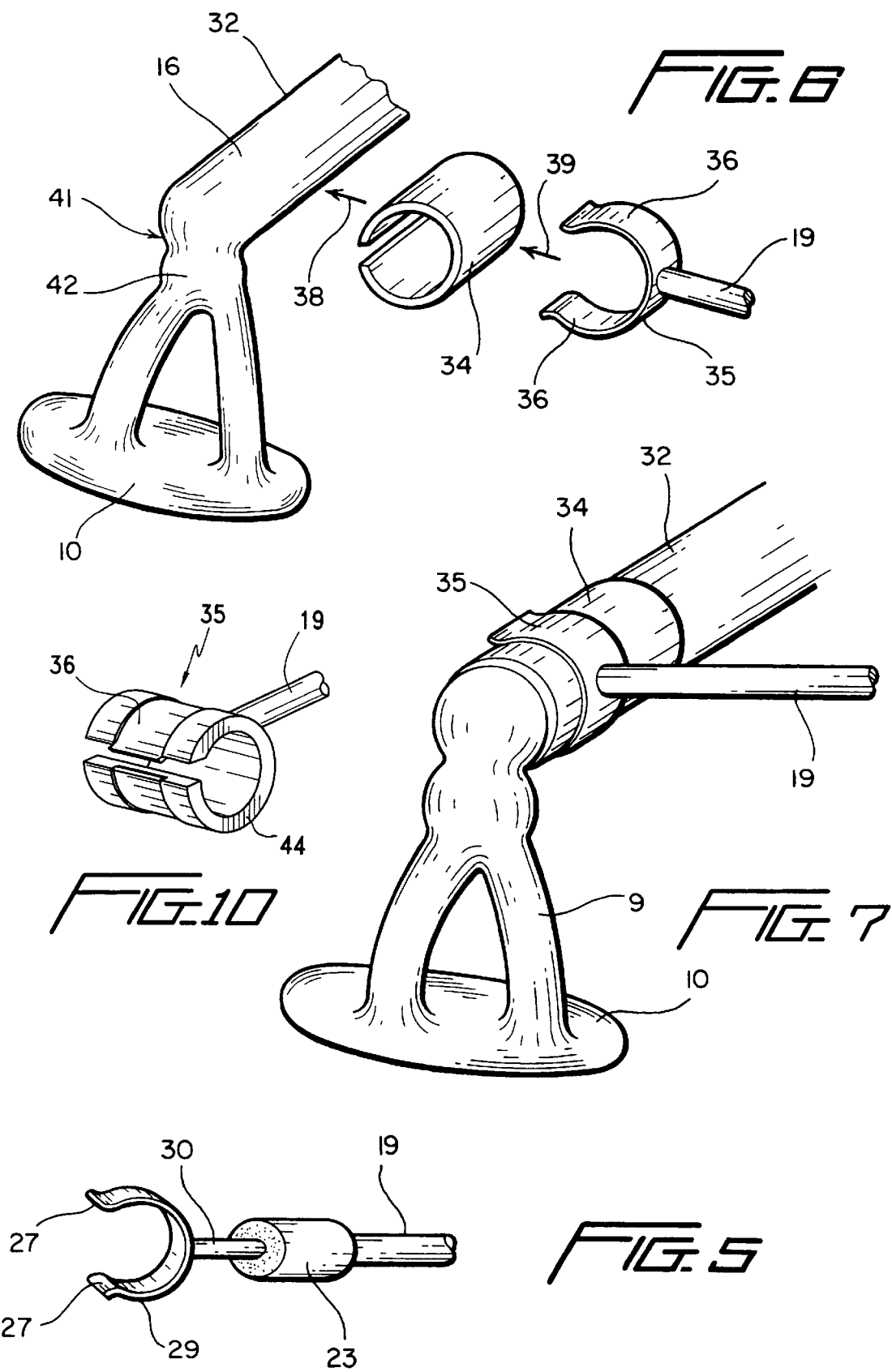

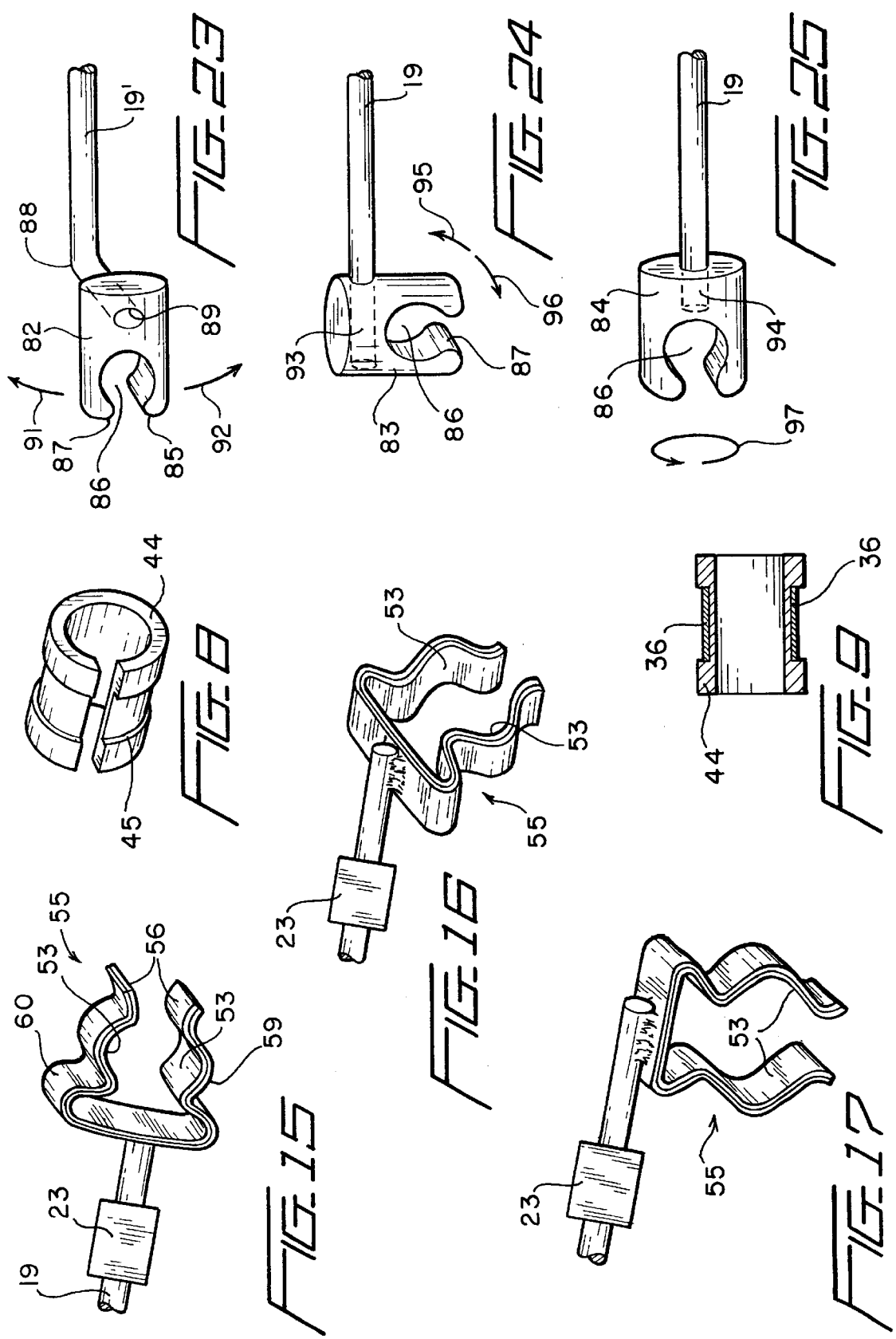

ARRANGEMENT FOR MECHANICAL COUPLING OF A DRIVER TO A COUPLING SITE OF THE OSSICULAR CHAIN

BACKGROUND OF THE INVENTION

1. Field of the Invention

The invention relates to an implantable arrangement for mechanical coupling of an output driver part of an active or passive hearing system to a preselected coupling site on the ossicular chain, the footplate of the stapes or a membrane which closes the round window or an artificial window in the cochlea, in the vestibulum or in the labyrinth (equilibrium organ), via a coupling arrangement which has a coupling element which can be connected, preferably by force-fit, to a preselected coupling site, the driver part being adapted to be excited to mechanical vibrations.

2. Description of Related Art

Partially implantable or fully implantable hearing systems for direct mechanical stimulation are known. In these hearing systems, the acoustic signal is converted into an electrical signal with a converter (microphone) and is amplified in an electronic signal processing stage, this amplified electrical signal is supplied to an implanted electromechanical converter with output-side mechanical vibrations which are supplied directly, i.e., with direct mechanical contact, to the middle ear or inner ear. This applies regardless of whether pure labyrinthine deafness with a completely intact middle ear or combined deafness (middle ear and inner ear damaged) is to be rehabilitated. Therefore, implantable electromechanical converters and processes for direct coupling of the mechanical converter vibrations to the intact middle ear or to the inner ear, respectively, for rehabilitation of pure labyrinthine deafness and also to the remaining ossicles of the middle ear in an artificially or pathologically altered middle ear for treatment of conductive deafness and their combinations have been described in the more recent scientific and patent literature.

Basically, all physical conversion principles can be used as electromechanical converter processes, such as electromagnetic, electrodynamic, magnetostrictive, dielectric, and piezoelectric. In recent years, various research groups have focused essentially on two of these processes: electromagnetic and piezoelectric. An outline of these converter versions can be found in Zenner and Leysieffer (HNO 1997 Vol. 45, 749–774).

In the piezoelectric process, mechanically direct coupling of the output-side converter vibrations to the middle ear ossicle or directly to the oval window is necessary. In the electromagnetic principle the force coupling, on the hand, can take place via an air gap ("contactless"), i.e., only one permanent magnet is placed by permanent fixation in direct mechanical contact with a middle ear ossicle. On the other hand, it is possible to dispose the entire converter within a housing (the coil and the magnet being coupled with the smallest possible air gap) and to transfer the output-side vibrations via a mechanically stiff coupling element with direct contact to the middle ear ossicle (Leysieffer et al. 1997 (HNO 1997, Vol. 45, pp. 792–800).

The patent literature contains some of the aforementioned versions of both electromagnetic and also piezoelectric hearing aid converters: U.S. Pat. Nos. 5,707,338 (Adams et al.), 5,554,096 (Ball), 3,712,962 (Epley), 3,870,832 (Fredrickson), 5,277,694 (Leysieffer et al.), 5,015,224 (Maniglia), 3,882,285 (Nunley), and 4,850,962 (Schaefer), International Patent Application publication Nos. WO 98/06235 (Adams et al.), WO 98/06238 (Adams et al.), WO 98/06236 (Kroll et al.) and WO 98/06237 (Bushek et al.), and published European Patent Application Nos. EP-A-0 984 663 (corresponding to commonly owned, U.S. Application Ser. No. 09/275,872) (Leysieffer), and EP-A-0 984 665 (corresponding to commonly owned U.S. Application Ser. No. 09/311,563) (Leysieffer).

The partially implantable piezoelectric hearing system of the Japanese group of Suzuki and Yanigahara presupposes, for implantation of the converter, the absence of the middle ear ossicles and an empty tympanic cavity in order to be able to couple the piezoelement to the stapes (Yanigahara et al.: Efficacy of the partially implantable middle ear in middle and inner ear disorders. Adv. Audiol, Vol. 4, Karger Basel (1998), pp. 149–159; Suzuki et al.: Implantation of partially implantable middle ear implant and the indication. Adv. Audiol., Vol. 4, Karger Basel (1988), pp. 160–166). Similarly, in the process of a partially implantable hearing system for those suffering from labyrinthine deafness according to U.S. Pat. No. 4,850,962 (Schaefer), basically, the incus is removed in order to be able to couple a piezoelectric converter element to the stapes. This also applies especially to other developments which are based on Schaefer technology and which are documented in the aforementioned disclosures (U.S. Pat. No. 5,707,338, and International Patent Application publication Nos. WO 98/06235, WO 98/06238, WO 98/06236, WO 98/06237).

Conversely, the electromagnetic converter of BALL ("Floating Mass Transducer FMT," U.S. Pat. Nos. 5,624,376 and 5,554,096) is fixed with titanium clips directly on the long process of the incus when the middle ear is intact. The electromagnetic converter of the partially implantable system of FREDRICKSON (Fredrickson et al.: Ongoing investigations into an implantable electromagnetic hearing aid for moderate to sever sensorineural hearing loss. Otolaryngologic Clinics of North America, Vol. 28/1 (1995), pp. 107–121) is mechanically coupled directly to the body of the incus when the ossicular chain of the middle ear is likewise intact. The same applies to the piezoelectric and electromagnetic converters of LEYSIEFFER (Leysieffer et al.: An implantable piezoelectric hearing aid converter for patients with labyrinthine deafness. HNO 1997/45, pp. 792–800, U.S. Pat. No. 5,277,694, and published European Patent Application Nos. EP-A-0 984 663 and EP-A-0 984 665). Also, in the electromagnetic converter system of MANIGLIA (Maniglia et al: Contactless semi-implantable electromagnetic middle ear device for the treatment of sensorineural hearing loss, Otolaryngologic Clinics of North America, Vol. 28/1 (1995) pp. 121–141), when the ossicular chain is intact, a permanent magnet is permanently fixed mechanically to the ossicular chain but is, however, mechanically driven via an air gap coupling by a coil.

In the described converter and coupling versions, basically, two implantation principles can be distinguished:

a) In the case of the one principle the electromechanical converter with its active converter element is located itself in the middle ear region in the tympanic cavity and the converter is directly connected there to an ossicle or the inner ear (U.S. Pat. Nos. 4,850,962, 5,015,225, 5,707,338, 5,624,376, 5,554,096, and International Patent Application publication Nos. WO 98/06235, WO 98/06238, WO 98/06236, and WO 98/06237).

b) In the other principle the electromagnetic converter with its active converter element is located outside of the middle ear region in an artificially formed mastoid cavity, the output-side mechanical vibrations are then transmitted to the middle or inner ear by means of mechanically passive coupling elements via suitable surgical accesses (the natural aditus ad antrum, opening of the chorda-facialis angle or via an artificial hole from the mastoid) (Fredrickson et al.: Ongoing investigations into an implantable electromagnetic hearing aid for moderate to severe sensorineural hearing loss. Otolaryngologic Clinic of North America, Vol. 28/1 (1995), pp. 107–121: U.S. Pat. No. 5,277,694; published European Application Nos. EP-A-0 984 663, EP-A-0 984 665).

In a) type versions, the converter can be made as a so-called "floating mass" converter, i.e., the converter element does not require any "reaction" via secure screwing to the skull bone, but it vibrates based on the laws of mass inertia with its converter housing and transmits these vibrations directly to a middle ear ossicle (U.S. Pat. Nos. 5,624, 376, 5,554,096, and 5,707,338, and International Patent Application publication no. WO 98/06236). On the one hand, this means that an implantable fixation system on the cranial vault can be advantageously omitted; on the other hand, this version disadvantageously means that bulky artificial elements must be placed in the tympanic cavity and their long-term stability and biostability are currently not known or guaranteed, especially in the case of temporary pathological changes of the middle ear (for example, otitis media). Another major disadvantage is that the converter together with its electrical supply line has to be transferred from the mastoid into the middle ear and must be fixed there using suitable surgical tools; this requires expanded access through the chorda facialis angle, and thus, entails a latent hazard to the facial nerve which is located in the immediate vicinity.

In the converter versions as per b), the converter housing with the implantable positioning and fixation systems is attached to the cranial vault (advantageous embodiment U.S. Pat. No. 5,788,711). Both in the partially implantable system in FREDRICKSON (Ongoing investigations into an implantable electromagnetic hearing aid for moderate to severe sensorineural hearing loss. Otolaryngologic Clinics of North America, Vo. 28/1 (1995), pp. 107–121) as well as in the fully implantable hearing system of LEYSIEFFER and ZENNER (HNO 1998, vol. 46, 853–863 and 844–852), when the vibrating driver part is coupled to the body of the incus, it is assumed for permanent and mechanically secure vibration transmission that the tip of the coupling rod which is placed in the laser-induced depression of the middle ear ossicle undergoes osseointegration over the long term, i.e., the coupling rod coalesces solidly with the ossicle and thus ensures reliable transmission of dynamic compression and tensile forces. However, this long-term effect is currently not yet scientifically proven or certain. Furthermore, in this type of coupling, in case of a technical converter defect, there is the disadvantage that decoupling from the ossicle to remove the converter can only be done with mechanically based surgical methods; this can mean considerable hazard to the middle ear and especially the inner ear.

The major advantage of these converter embodiments as per b), however, is that the middle ear remains largely free and coupling access to the middle ear can take place without major possible hazard to the facial nerve. One preferable surgical process for this purpose is described in U.S. Patent Application Ser. No. 09/168,079. Basic advantageous forms of passive coupling elements for transmission of the output-side converter vibrations from the mastoid to the middle ear or inner ear are described in U.S. Pat. Nos. 5,277,694 and 5,941,814 and in HNO 1998 Vol. 46, pp. 27–37 Lehner et al.: "Cold-flowing elements for coupling of an implantable hearing aid converter to the auditory ossicle or perilymph." The coupling elements are especially made of gold, preferably soft-annealed fine gold, in the form of a C-band for the long process of the incus, a band loop for the long process of the incus and a tiny bell for the head of the stapes, and these coupling elements can be coupled using instruments which are standard in ear surgery, and if necessary, they can also be detached again.

In both active and passive hearing systems, a large transmission bandwidth is desirable to be able to faithfully transmit music signals, for example, in addition to speech signals. In doing so, in addition to the spectral demands on the hearing system, the dynamic operating behavior also plays an important role when it is a matter or reproducing as faithfully as possible the time envelope curve behavior of an audio signal, especially for highly variable signal portions, such as plosives in speech discrimination and for pulse-containing portions in music transmission. Furthermore, for active hearing systems, frequency-independent mechanical deflection of the output driver part and of the coupling elements connected thereto at a constant voltage of the electromechanical converter generally is desirable. Known coupling elements in the vibration transmission path between the output driver part and the preselected coupling site, for example, in the form of metallic or ceramic coupling rods of an active hearing system or of prostheses produced from bio-ceramic materials in a passive hearing system, typically have a high resonance sharpness (high Q-factor): pronounced linear distorsions occur. A high mechanical quality can also occur on the side of the electromechanical converter. As a result, undesirable resonance phenomena can occur within the wide transmission range. This applies especially when the electromechanical converter is housed in the mastoid cavity, because in the relation of the size of the massive coupling element to the volume of the dynamic portions of the active converter element present in this case, a clear effect of the coupling element on the dynamic properties, and thus, on the entire transmission function of the converter system must be expected. It is known (International Patent Application publication WO 99/15111) that provisions can be made for attenuation in the transmission path between an active converter element of an active hearing system and a coupling site on the ossicular chain by inserting a flexible connection part, for example, in the form of a spring or a urethane strip, between the converter element and the coupling element which can be drivingly connected to the coupling site. The flexible connection part which sits between the coupling element and the active converter element provides for elastic coupling of the active converter element to the coupling element. It is furthermore known (Alaa El SEIFI: The Necrosed Incus in Stapedectomy Revision, Laryngoscope 106, April 1996, pp. 511–512) in cases in which a wire loop which has been provided for coupling a passive stapes prosthesis to an incus stump has become loose, to push a piece of hose made of Silastic® which is slit over part of its longitudinal dimension over the wire loop and the incus stump in order to press the wire loop in this way against the incus stump and to restore coupling between the two.

SUMMARY OF THE INVENTION

The object of this invention is to devise an implantable arrangement for mechanical coupling of an output driver part of an active or passive hearing system, the driver part being adapted to be excited to mechanical vibrations, and said arrangement having advantageous properties for transmission of vibrations from the output driver part to a preselected coupling site on the ossicular chain, the footplate of the stapes or a membrane which closes the round window or an artificial window in the cochlea, in the vestibulum or in the labyrinth (equilibrium organ), which arrangement promotes an optimum form of vibration of the footplate of the stapes or the aforementioned membrane and keeps the risk of damage to the natural structures in the region of the coupling site during and after implantation especially low.

Starting from a device of the type having an implantable arrangement for mechanical coupling of an output driver part of an active or passive hearing system, the driver part being excitable to mechanical vibrations, to a preselected coupling site on the ossicular chain, the footplate of the stapes or a membrane which closes the round window or an artificial window in the cochlea, in the vestibulum or in the labyrinth (equilibrium organ), via a coupling arrangement which has a coupling element which can be connected to a preselected coupling site, this object is achieved in accordance with the invention by the provision of an attenuator having entropy-elastic properties and, in the implanted state, resting against the coupling site.

An attenuator with entropy-elastic properties is defined here as an attenuator which has at least a certain entropic elasticity, optionally in combination with energy or steel elasticity (see in the regard DIN 7724). Entropic elasticity (also called rubber elasticity) means that elastic deformation proceeds essentially without a change of the internal energy. Entropic elasticity is due to the effort of large macromolecules to assume a form as random as possible.

The arrangement according to the invention provides in an especially simple, and at the same time, reliable manner for achieving a relatively flat frequency response for the deflection which occur at the preselected coupling site as a function of the vibrations of the output-side driver part. Another important advantage is that the coupling site, for example, of the ossicle is not "restrained" mainly in the direction of vibration of the driving converter, since such "restraint" can lead to a less than optimum form of vibration of the footplate of the stapes in the oval window. (One preferable form of vibration is a piston-like vibration of the footplate of the stapes perpendicular to its plane). Rather, the ossicle, as a result of the non-rigidity or pliability of the attenuator, sets itself (frequency-dependent) direction of vibration based on the dynamic properties of the intact middle ear. This advantage also applies to a non-intact, (partially) decomposed ossicular chain and coupling to the "remainder" of the chain facing the inner ear, and in the extreme case, also to only a residual stapes or only the footplate of the stapes since it is suspended by the so-called ligament (the elastic annular ligament which "holds" the stapes in the oval window). Moreover the attenuator effectively protects the coupling site against damage by the coupling element both during and also after implantation.

In another embodiment of the invention, the attenuator in the implanted state can be positioned at least partially between the coupling element and the coupling site. In doing so, the attenuator can be advantageously made as a molded part which in the implanted state at least partially surrounds part of the ossicular chain. As attenuator, however, there can also be provided a coating with entropy-elastic properties on the side of the coupling element which comes into contact with the coupling side.

According to a modified embodiment of the invention, the vibration transmission path has a coupling rod which is drivingly connected to the output driver part and a coupling element which can be drivingly connected to the preselected coupling site and which is attached to the coupling rod, the attenuator being made as a coating with entropy-elastic properties, which at least partially surrounds the coupling element, wherein in the implanted state, part of the coating is disposed between the coupling element and the coupling site.

In another modified embodiment of the invention, the vibration transmission path has a coupling rod which is drivingly connected to the output driver part and a coupling element which can be drivingly connected to the preselected coupling site and which is connected to the coupling rod, and the attenuator sits between the coupling rod and the coupling element. In doing so, it is practical for the attenuator to be located between the coupling rod and the coupling element. In particular, as the attenuator, an essentially cylindrical molding can be used which is provided with receivers for the coupling element-side end of the coupling rod and for the coupling rod-side end of the coupling element. But, this can also be done such that the coupling rod-side end of the coupling element surrounds the coupling element-side end of the coupling rod with the formation of a gap between these two ends and the gap is at least partially filled with a material which forms the attenuator with entropic elastic properties.

According to another embodiment of the invention, the coupling element itself is made as the attenuator. Thus, as the coupling element and the attenuator, a free end of a molded part with entropy-elastic properties can be inserted into the space between the stapes and the footplate of the stapes.

Especially cross-linked silicones or another implantable rubber-like material are suitable as the material for the attenuator.

The arrangement in accordance with the invention can be part of an active hearing system in which the output driver part is a vibratory part, especially a vibratory membrane, of an electromechanical hearing aid converter. The arrangement of the invention can, however, also be part of a passive hearing system, especially a partial or full middle ear prosthesis in which in the implanted state the eardrum is used as the output-side driver part.

Preferred embodiments of the arrangement in accordance with the invention are explained in detail below using the attached drawings.

BRIEF DESCRIPTION OF THE DRAWINGS

FIG. 5 is a perspective representation of a spring clamp which is provided as the coupling element and which is connected to the coupling rod via an attenuator as shown in FIG. 4;

FIG. 6 is an exploded perspective representation of an arrangement for coupling to a limb of the incus using an attenuator in the form of a piece of hose which has been slit lengthwise;

FIG. 7 is a perspective representation of the arrangement shown in FIG. 6 in the coupled state;

FIG. 8 is a perspective representation of an attenuator in the form of a sleeve which has been slit lengthwise;

FIG. 9 is a longitudinal section of the attenuator of FIG. 8 held by a spring clamp as shown in FIG. 10;

FIG. 10 is a perspective representation of the attenuator and a spring clamp shown in FIG. 8;

FIGS. 15 to 17 each show a modified attachment to a coupling rod for a spring clamp with a coating corresponding to FIGS. 13 and 14;

FIGS. 23 to 25 each show a perspective representation of a respective embodiment in which the coupling element itself is made as an attenuator;

FIG. 32 is a schematic perspective view of a passive middle ear prosthesis in accordance the invention.

DETAILED DESCRIPTION OF THE INVENTION

Figure 1:
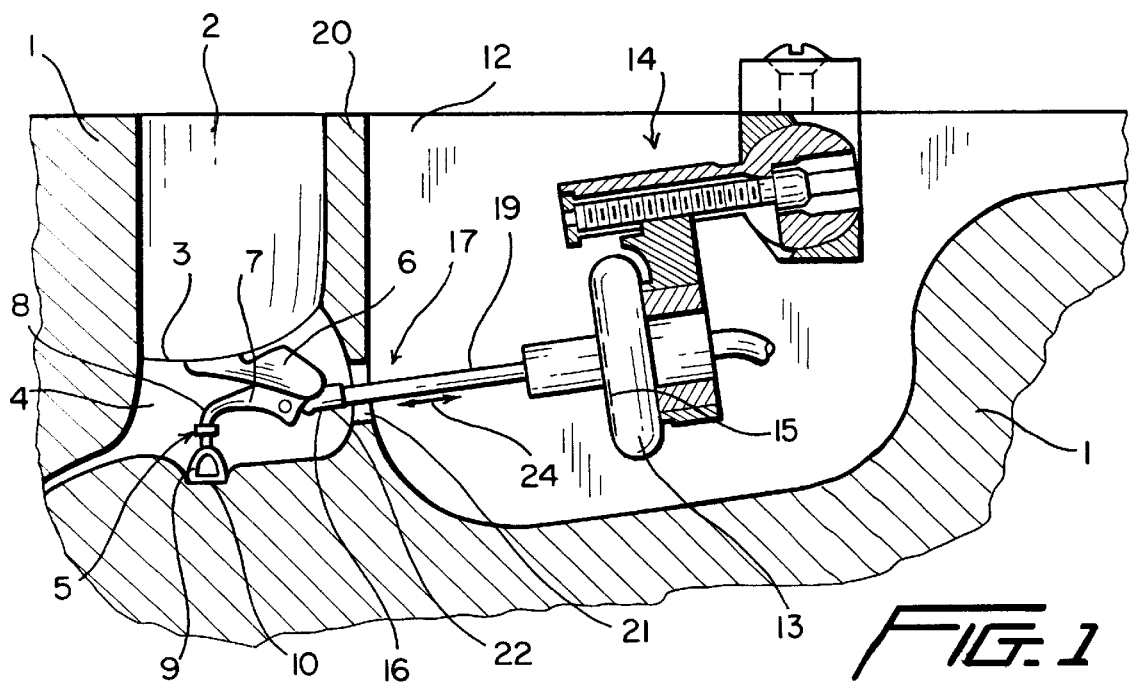
FIG. 1 is an enlarged schematic view of an implanted hearing aid converter with the coupling rod coupled to the ossicular chain.

FIG. 1 shows part of a human skull bone 1 with the auditory canal 2, the middle ear space (tympanic cavity) 4 which is separated therefrom by the eardrum 3, and the ossicular chain 5 which is located in the tympanic cavity. The ossicular chain 5 includes the malleus 6, the incus 7 with the long process 8 of the incus, and the stapes 9 with the footplate 10 of the stapes. In an artificial mastoid cavity 12, an electromechanical hearing aid converter 13 is fixed by means of a positioning and fixing system 14. The hearing aid converter 13 can be built, for example, as a piezoconverter for vibratory stimulation of the ossicular chain especially in the manner known from U.S. Pat. No. 5,277,694 and it is a component of at least one-partially implantable and preferably fully implantable hearing aid, for example a hearing aid of the type known from HNO 1997 Vol. 45, 749–774.

For mechanical coupling of an output driver part 15 of the hearing aid converter 13, which part is shown only schematically in FIG. 1 and which can be excited to mechanical vibrations, especially a vibratory membrane of this converter, to a preselected coupling sit 16 on the ossicular chain 5, for example, to the "smooth" body of the incus 7 from the mastoid side, there is a vibration transmission path in the form of a biocompatible, mechanically passive coupling arrangement 17. The coupling arrangement 17 is connected to the actively vibrational output driver part 15, and, in the implanted state, it adjoins the coupling site 16 with the coupling end which is the end opposite the hearing aid converter 13. When an electrical voltage is applied to the hearing aid converter 13, the coupling arrangement 17 is caused to execute vibratory oscillations in the axial direction of the coupling arrangement by means of the output driver part 15. As a result, the electrically converted audio signals which are picked up by an input-side converter (microphone) (not shown), after electronic amplification in an electronic module of the active hearing system, lead directly to mechanical deflections of the coupling arrangement 17. These deflections correspond to the acoustic information. The deflections of the coupling arrangement 17 are relayed to the ossicular chain 5 of the middle ear or to the stapes 9, the footplate 10 of the stapes or a membrane (not shown) which closes the oval or round window or an artificial window in the cochlea, in the vestibulum or in the labyrinth (equilibrium organ). The deflections of the coupling arrangement cause an audiological amplification effect for a corresponding design of the electronic preprocessing system.

Figure 2:
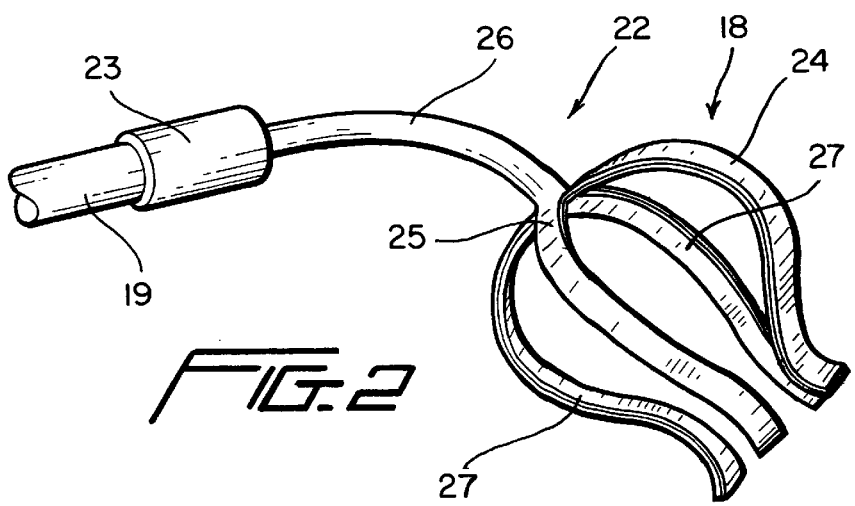
FIG. 2 shows, on a still larger scale, a perspective representation of the coupling element which is connected to the coupling rod of the hearing aid converter in FIG. 1 via an attenuator for coupling the hearing aid converter to the body of the incus.

In this embodiment the coupling arrangement 17 has a coupling rod 19 which is mechanically joined securely to the output driver part 15 and which in this embodiment has the shape of a straight cylinder essentially over its entire length. The coupling rod 19 extends, in the implanted state, from the mastoid cavity 12 into the tympanic cavity 4, preferably through a natural, if necessary artificially widened, bone opening (aditus ad antrum) 21 which is located in the rear wall 20 of the auditory canal. Furthermore, the coupling arrangement 17 includes a coupling element 22 which is shown in particular in FIGS. 2 and 3 and which is connected via a coupling 23 to the end of the coupling rod 19 which is remote from the hearing aid converter 13 and which forms a coupling end 18 of the coupling arrangement 17. In this embodiment, the coupling element 22 on the coupling end 18 has four spring arms 24 each of which having an end which all meet at a connection piece 25. The connection piece 25 is connected to a stalk 26.

A coating having entropy-elastic properties is provided between the coupling element 22 and the coupling site 16 as an attenuator 27. The coating is located on the inner side of the spring arms 24 so that, in the implanted state, the coating comes into contact with the coupling site 16. The coupling element 22, via the attenuator 27, grips the body of the incus 7 so that dynamic tension-compression force coupling of the coupling element 22 and the target ossicle (in the illustrated case the incus 7) occurs. The attenuator 27 is made of an entropy-elastic or rubber-elastic material, preferably a crosslined silicone. The attenuator 27 reduces the mechanical quality of the vibration transmission path 17 and thus increases the evenness of the deflection frequency response of the hearing system. Moreover, the attenuator 27 protects the coupling site 16 against damage by the preferably metallic spring arms 24 during and after implanting.

Figures 3, 4:
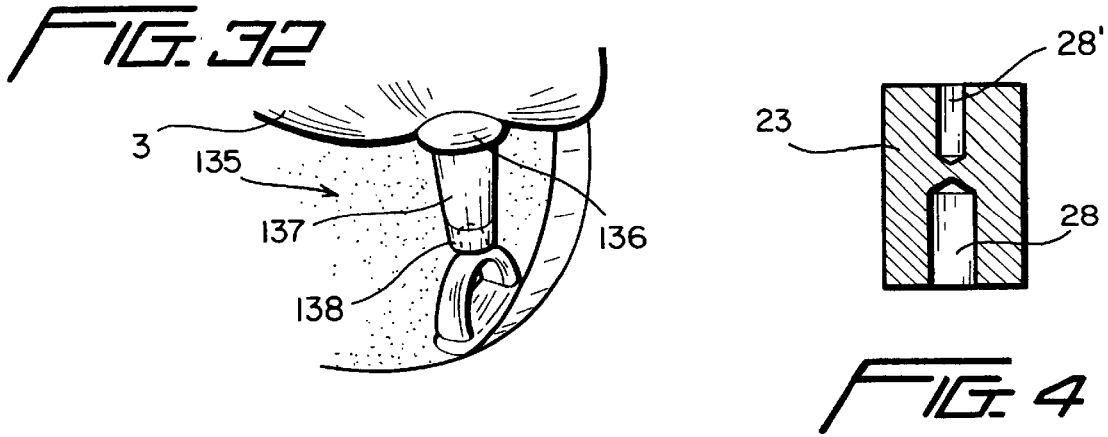
FIG. 3 is a perspective representation of the coupling element shown in FIG. 2 in the implanted state.
FIG. 4 is a longitudinal section of the attenuator of FIGS. 2 and 3.
Figure 3:
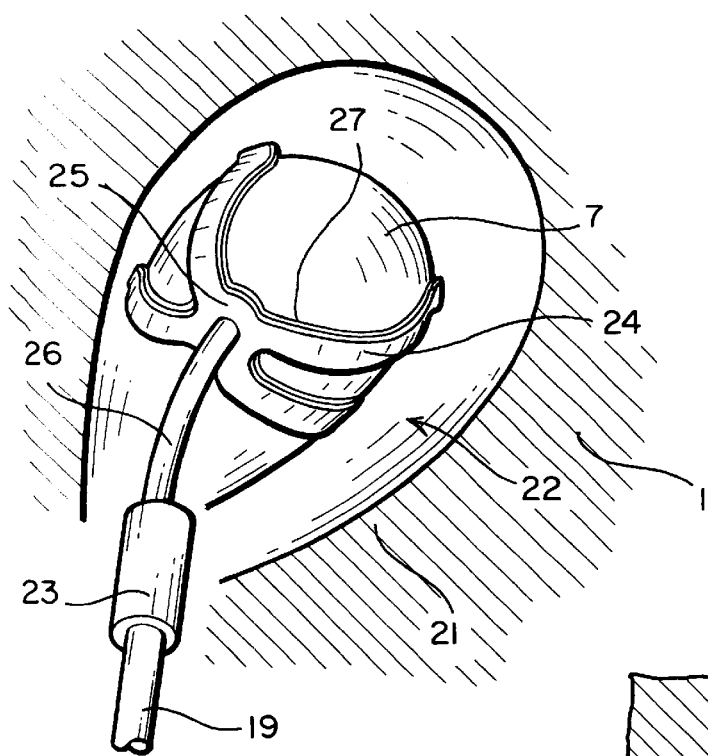

The coupling 23, which is shown in FIG. 4 on a larger scale, is an essentially cylindrical molded part. The coupling 23 has two recesses 28, 28' which extend axially and which are aligned with one another for holding the coupling element end of the coupling rod 19 and the coupling rod of the stalk 26 of the coupling element 22. These ends, in the implanted state, are securely joined to the coupling 23. For example, they can be pressed and/or cemented into the recesses 28, 28', thus establishing a force-fit connection.

In the embodiment of FIG. 5, the coupling element 29 is made as a twin-arm spring clamp which has a stalk 30 and which is suited, for example, for coupling to the long process of the incus 32 (FIG. 6). Also in this case, the coupling 23 is used as the connecting element between the coupling rod 19 and the coupling element 29, the free ends of the coupling rod 19 and the stalk 30 being inserted into the recesses 28, 28' of the coupling 23. The coupling element 29, on its side facing the coupling site 16, has a coating which acts as the attenuator 27 analogously to the above explained coating of the spring arms 24.

FIGS. 6 and 7 show an embodiment in which an attenuator 34 is made as a molded part, and in the implanted state, lies between the coupling site 16 and the coupling element 35 and at least partially surrounds part of the ossicular chain, for example, the long process 32 of the incus. The coupling element 35, in this example, corresponds to the coupling element 29 of FIG. 5 with the exception that the spring clamp which is provided with two spring arms 36 is attached directly to the coupling rod 19 and the spring arms 36 have no coating 27. The molding which forms the attenuator 34 is a piece of hose which has been slit lengthwise and which is made of an entropy-elastic or rubber-elastic material, preferably a silicone resin. In the course of implantation, first the attenuator 34 is placed on the pertinent part of the ossicular chain (arrow 38 in FIG. 6). Then the coupling element 35 is pushed onto the attenuator 34 by moving the coupling rod 19 forward (arrow 39 in FIG. 6), the attenuator 34 at the same time protecting the coupling site 16 against damage by the spring arms 36 of the coupling element 35.

FIGS. 6 and 7 show the incudo-stapedial joint at 41, the head of the stapes at 42, and the footplate of the stapes at 10.

FIGS. 8 to 10 shown an embodiment of an attenuator 44 which largely corresponds to the embodiment as shown in FIGS. 6 and 7. The molded part which forms the attenuator 44, in this case, is a sleeve which has been slit lengthwise (or formed with a longitudinal slot) and which is made of an entropy-elastic or rubber-elastic material, preferably silicone resin. This sleeve is slipped onto the pertinent part of the ossicular chain in the area of the coupling site 16, similarly to the piece of hose in FIGS. 6 and 7. The attenuator 44 has a circumferentially extending groove 45 which is located between the axial ends of the sleeve, and into which the spring arms 36 of the coupling element 35 are inserted. The groove 45 prevents the spring arms 36 from axially slipping off of the attenuator 44.

Figure 11:
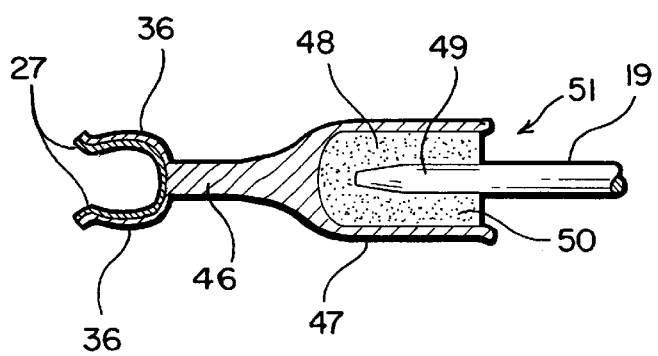
FIG. 11 is a longitudinal section of a coupling element which is connected to a coupling rod via a modified embodiment of the attenuator.
Figure 12:
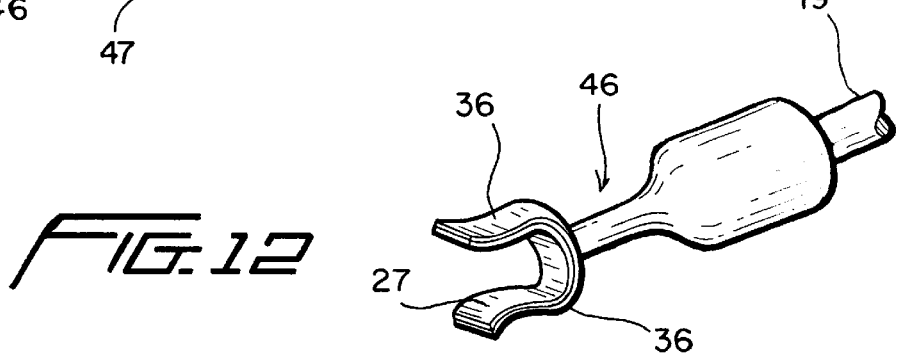
FIG. 12 is a perspective representation of the arrangement shown in FIG. 11.

FIGS. 11 and 12 shown another embodiment of an arrangement in which the attenuator as shown in FIG. 5 is made as a coating 27 on the spring arms 36 of a coupling element 46. The coupling element 46 is made cup-shaped in the area of its coupling rod end 47. The coupling element end 49 of the coupling rod 19 is inserted into the cavity 48 of the cup-shaped end such that a gap 50 is formed between them, i.e., without the coupling rod 19 touching the coupling element 46. The gap 50 can be filled with an entropy-elastic or rubber-elastic material which forms an additional attenuator 51. It goes without saying that, conversely, the coupling element end of the coupling rod can be cup-shaped and into which a part of the coupling element which corresponds to the stalk 26 of the coupling element 22 or a part which corresponds to the stalk 30 of the coupling element 29 is inserted.

Figure 13:
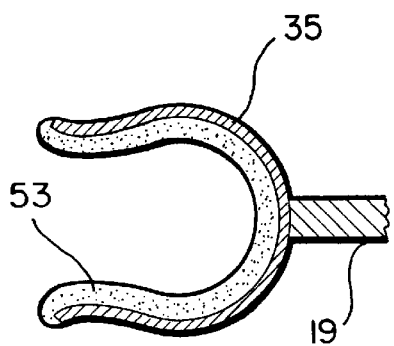
FIGS. 13 and 14 are, respectively, a lengthwise section and a perspective view of a coupling element in the form of a spring clamp with a coating which acts as the attenuator.
Figure 14:
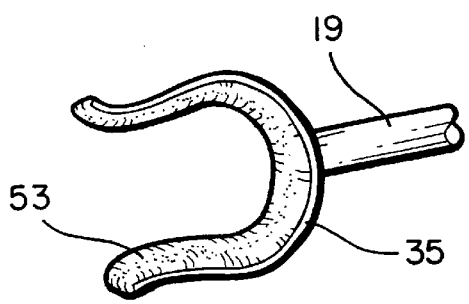

In the embodiment shown in FIGS. 13 and 14 there is also a coating with entropy-elastic properties as the attenuator 53 which is located between the coupling element 35 and the coupling site 16. The coating is again located on the side of the coupling element 35 which, in the implanted state, comes into contact with the coupling sit 16. In the case of this embodiment, analogously to the embodiment shown in FIGS. 6 and 7, the coupling rod 19 is attached directly to the coupling element 35, for example, welded to it.

FIGS. 15, 16 and 17 show a modified form of coupling element 55 in the form of a spring clamp with two spring arms 56. The spring arms 56 differ from the spring arms 36 essentially in that, in addition to the section 59 which surrounds one part of the ossicular chain, they have a corrugated spring section 60. The spring section 60 imparts to the coupling element 55 a certain energy elasticity which can be of benefit mainly for coupling to the sensitive structure of the ossicular chain. Depending on the location of the coupling site 16, the spring arms 56 can be aligned differently with reference to the coupling rod 19, as is apparent from FIGS. 15 to 17. Between the coupling rod 19 and the coupling element 55, a coupling 23 can be inserted in the manner shown. On at least the parts of the spring arms 56 which come into contact with the coupling site 16 there is provided as the attenuator a coating 53 having entropy-elastic properties, similarly as in FIGS. 13 and 14.

Figure 18:
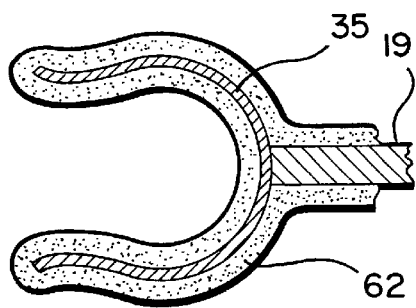
FIGS. 18 and 19 are, respectively, a longitudinal section and a perspective view of a coupling element in the form of a spring clamp with a jacket which acts as the attenuator.
Figure 19:
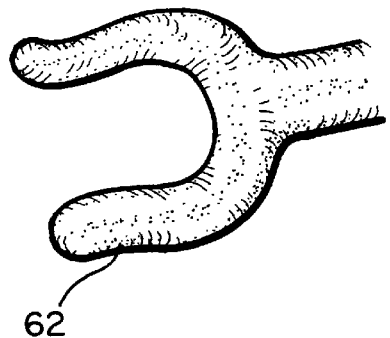

In the case of the embodiment of FIGS. 18 and 19, the coupling element 35 which is attached to the coupling rod 19 is jacketed by a coating 62 with entropy-elastic properties. The coating 62 can be produced, for example, by immersion silicon coating, and the coating forms an attenuator which lies between the coupling element 35 and the coupling site 16. In addition, the coating 62 protects the pertinent part of the sensitive ossicular chain in the coupling process.

Figure 20:
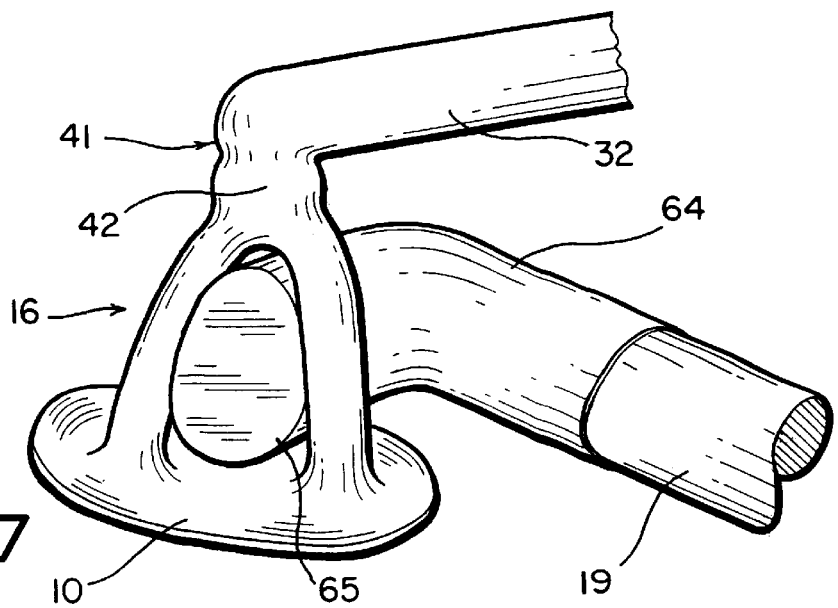
FIG. 20 is a perspective representation of a coupling element which is made as an attenuator.

FIG. 20 shows an embodiment in which the coupling element itself has a portion that serves as an attenuator. Here, on the end of the coupling rod 19 which faces the coupling site 16, a molded part made of a material with entropy-elastic properties, for example, silicone resin, is attached. The molding 64 can, as shown, have the shape of an bent circular cylinder; its diameter is, for example, approximately equal to the diameter of the coupling rod 19. The free end 65 of the molded part 64 is inserted into the free space between the stapes 9 and the footplate 10 of the stapes when the arrangement is implanted.

Figure 21:
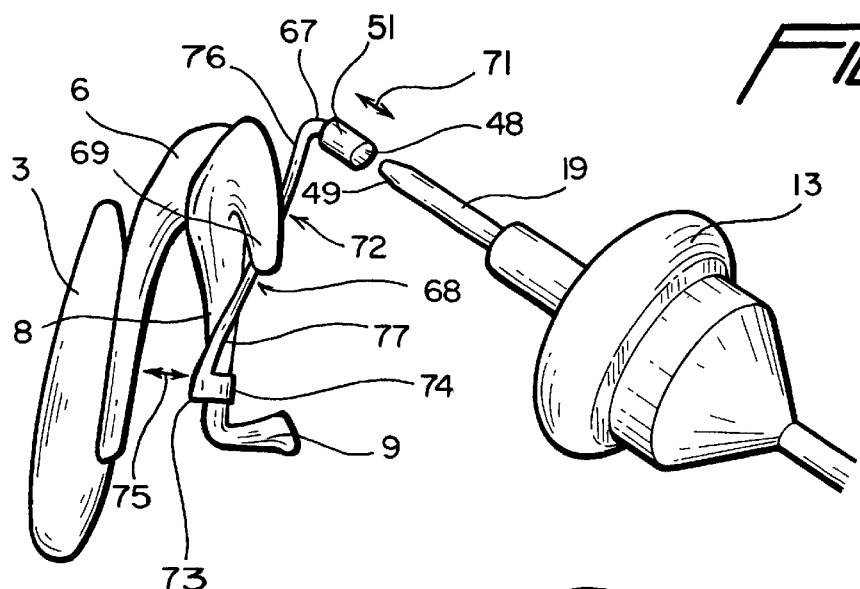
FIGS. 21 and 22 are perspective representations of two other embodiments of coupling element with attenuators.

FIG. 21 shows an embodiment in which, in the assembled state, the free end 49 of the coupling rod 19 is inserted into a cavity 48, as shown in FIG. 11, which is provided on the coupling rod end 67 of a coupling element 68. The coupling rod 19 and the coupling element 68 are connected via an additional attenuator 51 in the manner of FIG. 11. The coupling element 68 is made as a twin-arm lever which is supported in a middle area on the short process 69 of the incus. If, by means of the coupling rod 19, the coupling rod end 67 is caused to move as shown by the double arrow 71, the coupling element 68 swivels around a pivot 72 which is determined by the short process 69 of the incus. In this way, the other end 73 of the coupling element 68 which engages the long process 8 of the incus via a spring clamp 74 or the like and an attenuator in the form of a coating 53 (FIGS. 13 and 14) or 62 (FIGS. 18 and 19) is moved as shown by the double arrow 75. By corresponding dimensioning of the relative lengths of the arms 76 and 77 of the coupling element 68, a desired lever ratio can be adjusted. The embodiment of FIG. 21 can be modified among others such that there is solid coupling between the coupling rod 19 and the coupling element 68.

Figure 22:
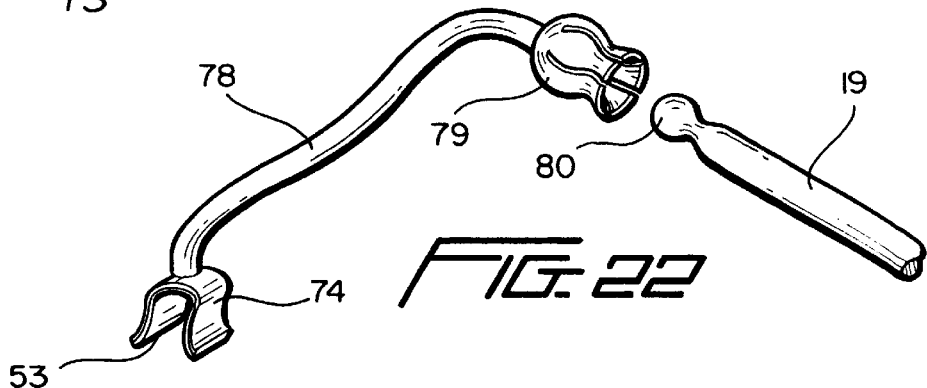

In the case of the embodiment shown in FIG. 22, on the coupling rod end of a coupling element 78 which is similar to the coupling element 68, there sits a slotted ball receiver 79. The coupling rod 19 bears on its coupling element end a spherical head 80 which fits into the ball receiver 79 and then forms a ball joint together with the ball receiver 79. This ball joint allows limited swivel motion of the coupling rod 19 relative to the coupling element 78. A spring clamp 74 which is attached to the other end of the coupling element 78 is provided, for example, with a coating 53 of the type explained in connection with to FIGS. 13 and 14 to form the attenuator.

FIGS. 23, 24, and 25 show other embodiments of the coupling elements 82, 83 and 84 which themselves form an attenuator and which are each made as a cylinder, for example, a straight cylinder, and are made of a material with entropy-elastic properties, for example, silicone. The coupling element 82, 83 and 84 each have a receiving opening 86 near their one axial end 85 which is aligned perpendicularly to the cylinder axis for the target ossicle. The receiving opening 86 is connected to the cylinder end 85 via a narrowed passage 87. The passage 87 is preferably rounded towards the cylinder end 85 and it is elastically flared when the coupling element is pushed onto the target ossicle.

In the embodiment shown in FIG. 23 there is a coupling rod 19' which at its coupling element end 88 is bent at a right angle. The coupling rod end 88 fits into a hole 89 of the coupling element 82 which runs parallel to the receiving opening 86, preferably with a fit such that the coupling element 82 can swivel in the direction of the arrows 91 and 92 around the end 88 of the coupling rod.

The embodiments of FIGS. 24 and 25 differ from the embodiment shown in FIG. 23 in that there is a straight coupling rod 19. In the case of FIG. 24 the coupling element-side end of the coupling rod 19 fits into a hole 93 of the coupling element 84, a hole which is aligned perpendicular to the receiving opening 86 and to the cylinder axis, and in the case of FIG. 25 into a hole 94 of the coupling element 84 a hole which is aligned with the cylinder axis. Preferably, the fits are selected such that the coupling elements 83, 84 can swivel around the coupling rod end in the direction of the arrows 95, 96 and 97.

Figure 26:
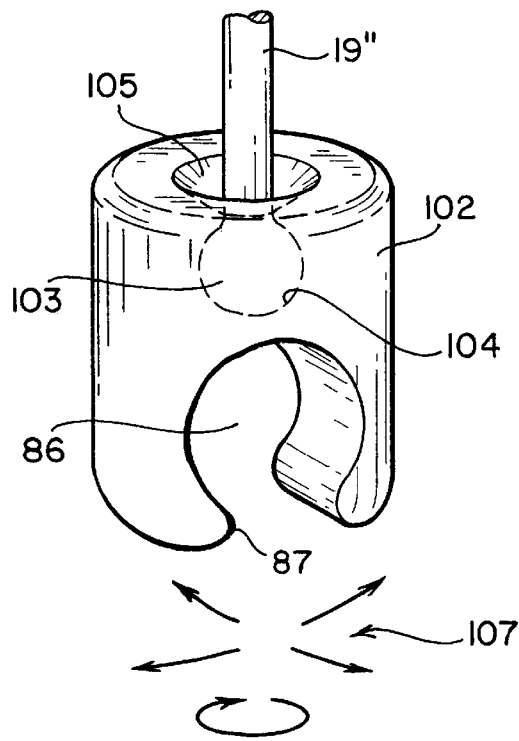
FIGS. 26 to 29 each show a perspective representation of a respective embodiment in which the coupling element, in addition to the attenuator, is connected to a coupling rod via a ball joint.
Figure 27:
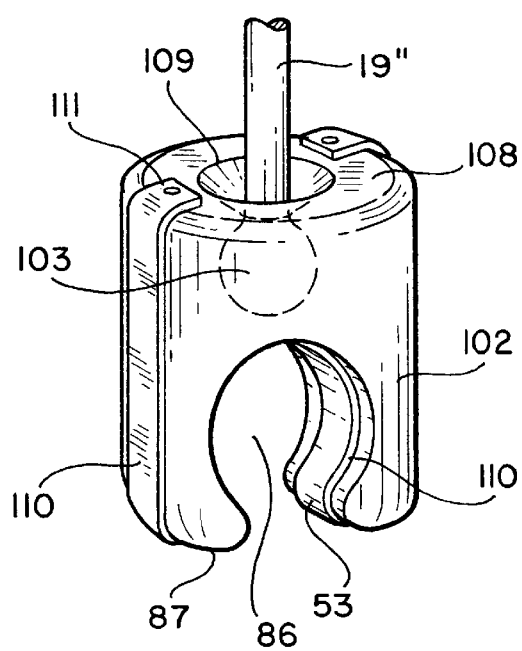

In the embodiments of FIGS. 26 and 27, as well, there is a cylindrical coupling element 102 which itself forms an attenuator and which is made of a material with entropy-elastic properties, for example, cross-linked silicone. The embodiment as shown in FIG. 26 is largely similar to the embodiment of FIG. 25. However, the coupling rod 19" is provided on its coupling element end with a ball 103 which fits into a ball receiver 104 of the coupling element 102. The ball 103 and the ball receiver 104 jointly form a ball joint. In the axial direction of the coupling element 102, a recess 105 which widens outwardly in the manner of a funnel adjoins the ball receiver 104. This formation makes it possible to swivel and turn the coupling element 102 in all spacial directions with reference to the coupling rod 19" in the manner illustrated by the group 107 of arrows.

In the embodiment as shown in FIG. 27, the coupling element 102 on the side facing away from the passage 87 bears a cover 108, preferably a metal cover. The cover 108 has an opening 109 which is aligned with the recess 105 and which has a diameter which is less than the diameter of the ball 103. In this way, the cover 108 prevents loss of the ball 103 and thus precludes unintentional separation of the coupling rod 19" and the coupling element 102. Furthermore, there is a preferably metallic spring clamp 110 which surrounds the coupling element 102 on diametrically opposite sides and which adjoins the end faces of the coupling element 102 and the opposite insides of the receiving openings 86 and the passage 87 or is admitted into these end faces and/or insides. The ends of the spring clamp 110 are connected to the cover 108, such as by being welded at 111. At least the part of the surface of the spring clamp 110 adjoining the target ossicle, in the implanted state, is provided with a coating 53 that has entropy-elastic properties. This coating forms an additional attenuator with a protective function for the target ossicle.

Figure 28:
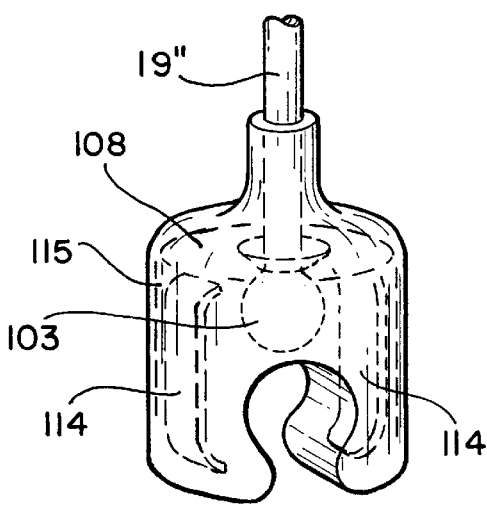

FIG. 28 shows an embodiment similar to that of FIG. 27 in which, however, elastic, preferably metallic, clips 114 are sealed into a coupling element 115 of a material with entropy-elastic properties, for example, silicone. In the illustrated embodiment, the material of the coupling element 115 which is adapted to constitute the attenuator also surrounds part of the coupling rod 19' on the side of the cover 108 facing away from the ball 103. In a suitable choice of this material and suitable wall thicknesses in the area of the coupling rod, not only in turning of the coupling element 115 around the axis of the coupling rod 19" possible, but also mutual swiveling of the coupling element and the coupling rod. The clips 114 can be welded to the cover 108 on one end. The clips 114 can, however, also be part of a spring clamp with a cover 108 seated on its middle bridge. Furthermore, the cover and the clips can be connected to one another in one piece.

Figure 29:
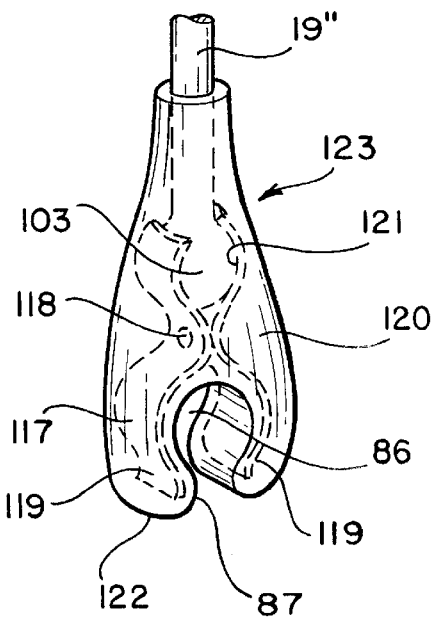

In the modified embodiment as shown in FIG. 29, as a coupling element 117, there is an elastic clamp consisting of two corrugated spring arms 119 which are welded together at 18. The coupling element 117 is sealed into a jacket 120 of a material with entropy-elastic properties, for example, silicone, the jacket acting as an attenuator. The spring arms 119 on the one side of the connection site 118 form a ball receiver 121 for the ball 103 of the coupling rod 19", and on the other side of the connection site, together with the jacket 120, form the spreadable passage 87 and the receiving opening 86 for the target ossicle. The coupling element 117 together with the jacket 120 can turn and swivel relative to the coupling rod 19". The passage 87 is located on the face side 122 of the body 123 comprising the coupling element and its jacket, i.e., the side facing away from the coupling rod 19".

Figure 30:
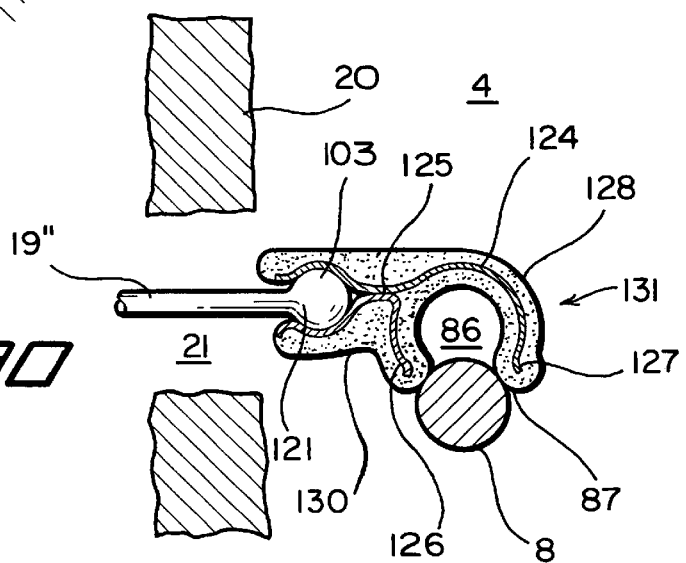
FIGS. 30 and 31 depict attachment and operation of another embodiment in which the coupling element, in addition to the attenuator, is connected to a coupling rod via a ball joint.
Figure 31:
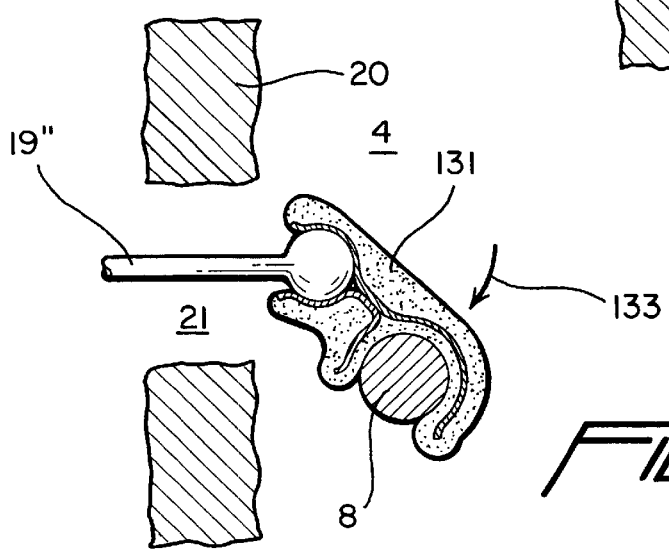

The embodiment as shown in FIGS. 30 and 31 is largely similar to that of FIG. 29. In this case as well, there is a coupling element 124 which is formed by two spring arms 126 and 127 which are connected to one another at 125, preferably by welding, and which are sealed into a jacket 128 which acts as an attenuator and which is made of a material with entropy-elastic properties, for example, silicone. The spring arms 126, 127 form the ball receiver 121 for the balls 103 of the coupling rod 19" and, together with the jacket 128, they form the spreadable passage 87 and the receiving opening 86 for the target ossicle 8. In contrast to the embodiment of FIG. 29, the passage 87 is located on a side surface 130 of the body 131 which is comprised of the coupling element 124 and its jacket 128.

The body 131 can be inserted into the middle ear space 4 through the opening 21 in the rear wall 20 of the auditory canal by means of the coupling rod 19" and positioned such that the spreadable passage 87 is aligned with the target ossicle, for example, the long process 8 of the incus, corresponding to FIG. 30. Then the body 131 is pressed down and thus swiveled with reference to the coupling rod 19" in the direction of arrow 133 in FIG. 31 until the target ossicle is positioned within the receiving opening 86 thus widening the passage 87. In this way reliable coupling to the target ossicle is achieved.

As the material for the coupling rod, all known biocompatible metals and their alloys can be used, mainly implantable titanium, especially pure titanium with a purity of greater than 99.6%. In addition, among others, platinum, niobium, or tantalum or alloys of titanium, platinum, niobium or tantalum are well suited. Optionally, the coupling rod can also consist of an implantable ceramic material, especially aluminum oxide. The spring arms, spring clamps and clips of the coupling elements can be made of the same metals and metal alloys as the coupling rod. For the coupling rod and the coupling elements, there can also be used long-term implantable plastics, such as, among others, cross-lined silicones, polyurethanes, PTFE, FEP, polycarbonates and the like which optionally can be fiber reinforced, especially carbon fiber reinforced.

FIG. 32 schematically shows an implantable passive hearing system in which the eardrum 3 is used as the output driver part which can be excited to mechanical vibrations. Adjacent to the eardrum 3 is a TORP prosthesis (total ossicular replacement prosthesis) designated 135, with a head 136 which has a rounded surface. The head 136 is adjoined by a shaft 137 which can be integrally connected to the head 136. The head 136 and the shaft 137 can be made of an implantable metallic or ceramic material. The end of the shaft 137 remote from the head 136 is coupled to the head 42 of the stapes via an attenuator 138 which has entropy-elastic properties and which is made preferably of cross-linked silicone.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

What is claimed is:

1. An implantable device for mechanical coupling of a mechanically vibratable output driver part of an at least partially implantable hearing system to a preselected coupling site on an inner or middle ear part of a patient via a coupling arrangement, the coupling arrangement comprising:
   a coupling element which is connectable to the preselected coupling site; and
   an attenuator with entropy-elastic properties which, when implanted, lies at least partially between the coupling element and the preselected coupling site.

2. A device as claimed in claim 1, wherein the attenuator is adapted to at least partially surround part of the ossicle chain in the implanted state.

3. A device as claimed in claim 1, wherein the attenuator is a molded part.

4. A device as claimed in claim 3, wherein the molded part is a sleeve which has a longitudinal slit.

5. A device as claimed in claim 4, wherein the sleeve has a peripherally extending groove which is located between axial ends of the sleeve and into which the coupling element is inserted.

6. A device as claimed in claim 1, wherein the attenuator is a piece of hose which has a longitudinal slit.

7. A device as claimed in claim 1, wherein the attenuator is a coating with entropy-elastic properties on a side of the coupling element which, in the implanted state, will come into contact with the preselected coupling site.

8. A device as claimed in claim 1, wherein the attenuator is a coating with entropy-elastic properties which at least partially surrounds the coupling element.

9. A device as claimed in claim 1, wherein the attenuator is formed by part of the coupling element itself.

10. A device as claimed in claim 9, wherein the part of the coupling element forming the attenuator is a molded part having entropy-elastic properties, an end of which is adapted to be insertable into a space between the stapes and the footplate of the stapes of the patient's ear.

11. A device as claimed in claim 9, wherein the part of the coupling element forming the attenuator has an at least roughly cylindrical shape.

12. A device as claimed in claim 11, wherein the part of the coupling element forming the attenuator has an opening adapted to receive a target ossicle and into which the target ossicle is insertable via a spreadable passage.

13. A device as claimed in claim 1, wherein the coupling arrangement has a coupling rod to which the coupling element is connected in at least a rotatable manner.

14. A device as claimed in claim 13, wherein connection between the coupling element and the coupling rod is a ball joint connection.

15. A device as claimed in claim 1, wherein the attenuator is made of a material with entropy-elastic properties from the group consisting of cross-linked silicone, rubber or elastomeric materials.

16. A device as claimed in claim 1, wherein the output driver part is a vibratory part of an electromechanical hearing aid converter and forms part of an active hearing system.

17. A device as claimed in claim 1, wherein the output driver part is part of a passive hearing system in which the eardrum is used as the output driver part in the implanted state.

18. A device as claimed in claim 1, wherein the coupling part comprises an elastic clamping member.

19. A device as claimed in claim 18, wherein the elastic clamping member is connected to a rod member via the attenuator.

20. A device as claimed in claim 18, wherein the attenuator is a coating with entropy-elastic properties on a side of the elastic clamping member which, in the implanted state, will come into contact with the coupling site.

* * * * *